(12) United States Patent
Borbély et al.

(10) Patent No.: US 9,283,285 B2
(45) Date of Patent: Mar. 15, 2016

(54) STABLE NANOCOMPOSITION COMPRISING DOCETAXEL, PROCESS FOR THE PREPARATION THEREOF, ITS USE AND PHARMACEUTICAL COMPOSITIONS CONTAINING IT

(71) Applicant: BBS Nanotechnology Ltd., Debrecen (HU)

(72) Inventors: János Borbély, Debrecen (HU); Zsuzsanna Csikós, Nyirbátor (HU); Krisztina Kerekes, Göd (HU)

(73) Assignee: BBS Nanotechnology Ltd., Debrecen (HU)

( * ) Notice: Subject to any disclaimer, the term of this patent is extended or adjusted under 35 U.S.C. 154(b) by 0 days.

(21) Appl. No.: 14/228,540

(22) Filed: Mar. 28, 2014

(65) Prior Publication Data

US 2014/0294966 A1   Oct. 2, 2014

Related U.S. Application Data

(60) Provisional application No. 61/805,981, filed on Mar. 28, 2013.

(51) Int. Cl.
*A61K 47/48* (2006.01)
*A61K 31/337* (2006.01)

(52) U.S. Cl.
CPC ........... *A61K 47/4823* (2013.01); *A61K 31/337* (2013.01); *A61K 47/48076* (2013.01);
(Continued)

(58) Field of Classification Search
CPC .................... A61K 47/4823; A61K 47/48853; A61K 31/337

USPC ......... 424/489, 490, 493, 497, 499; 977/773, 977/788
See application file for complete search history.

(56) References Cited

U.S. PATENT DOCUMENTS

| 7,976,825 B2 | 7/2011 | Borbely et al. |
| 8,007,768 B1 | 8/2011 | Sung et al. |

(Continued)

FOREIGN PATENT DOCUMENTS

| CN | 102813937 A | * 12/2012 |
| CN | 102813937 A | * 12/2012 |
| WO | 00/66090 A1 | 11/2000 |

*Primary Examiner* — Jane C Oswecki
(74) *Attorney, Agent, or Firm* — Jason D. Voight

(57) ABSTRACT

A nanoparticulate composition is disclosed for the targeted therapeutic treatment of tumors. The stable self assembled nanocomposition according to the invention comprises (i) a carrier and targeting system comprising an optionally modified polyanion, and optionally a polycation, which may also be modified; at least one targeting agent which is linked to either the polycation/modified polycation or the polyanion/modified polyanion, or both or to the surface of the nanoparticle; (ii) an active compound selected from the group of docetaxel and its pharmaceutically acceptable salts and derivatives especially its hydrates, especially docetaxel trihydrate and docetaxel trihydrate monohydrochloride; and optionally (iii) at least one complexing agent, a metal ion and a stabilizer/formulating agent, or a PEGylating agent. The present invention furthermore relates to a process for the preparation of the above-mentioned composition, the therapeutic uses thereof, and pharmaceutical compositions containing the nanocomposition according to the invention.

21 Claims, 7 Drawing Sheets

Figure 1:
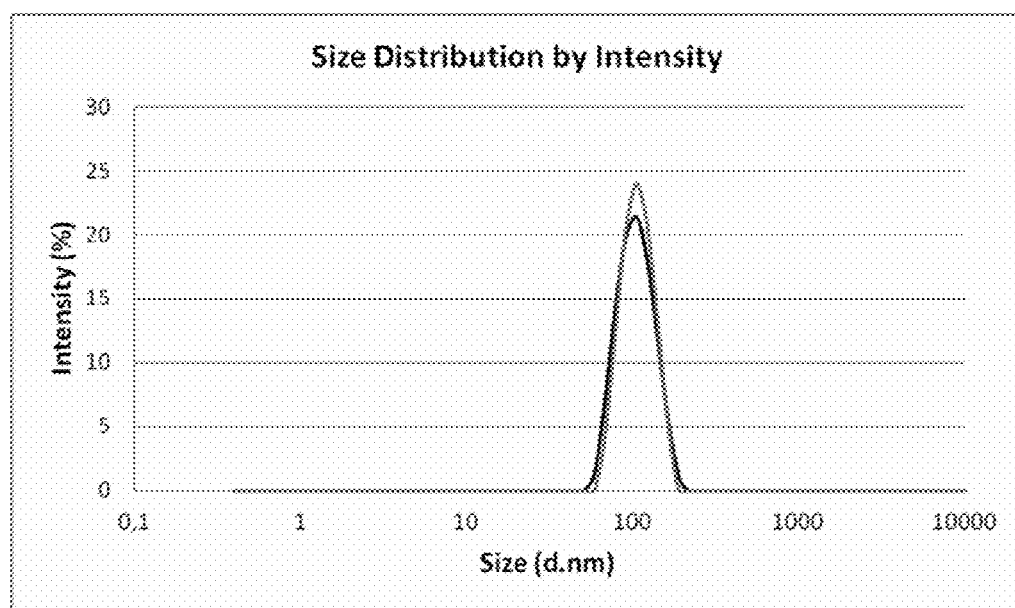

(52) U.S. Cl.
CPC ..... *A61K47/48107* (2013.01); *A61K 47/48853* (2013.01); *A61K 47/48907* (2013.01); *A61K 47/48923* (2013.01)

(56) References Cited

U.S. PATENT DOCUMENTS

| | | | |
|---|---|---|---|
| 9,132,098 B2* | 9/2015 | Borbely | A61K 9/5146 |
| 2006/0073210 A1 | 4/2006 | Sung et al. | |
| 2008/0193547 A1* | 8/2008 | Borbely | A61K 9/5146 424/499 |
| 2009/0004118 A1* | 1/2009 | Nie | A61K 47/48076 424/9.35 |
| 2010/0278725 A1 | 11/2010 | Liu et al. | |
| 2014/0294967 A1* | 10/2014 | Borbely | A61K 31/337 424/489 |
| 2014/0294983 A1* | 10/2014 | Borbely | A61K 9/5146 424/497 |
| 2014/0296173 A1* | 10/2014 | Borbely | A61K 31/704 514/34 |

* cited by examiner

Components of docetaxel loaded nanoparticles

STABLE NANOCOMPOSITION COMPRISING DOCETAXEL, PROCESS FOR THE PREPARATION THEREOF, ITS USE AND PHARMACEUTICAL COMPOSITIONS CONTAINING IT

This application claims priority to U.S. provisional application Ser. No. 61/805,981, filed Mar. 28, 2013, the entire disclosure of which is hereby incorporated by reference herein.

FIELD OF THE INVENTION

The present invention relates to a nanoparticulate composition for the targeted therapeutic treatment of tumours. The stable self assembled nanocomposition according to the invention comprises (i) a carrier and targeting system comprising an optionally modified polyanion, and optionally a polycation, which may also be modified; at least one targeting agent which is linked to either the polycation/modified polycation or the polyanion/modified polyanion, or both, or to the surface of the nanoparticle; (ii) an active compound selected from the group of docetaxel and its pharmaceutically acceptable salts and derivatives especially its hydrates, especially docetaxel trihydrate and docetaxel trihydrate monohydrochloride; and optionally (iii) at least one complexing agent, a metal ion and a stabilizer/formulating agent or a PEGylating agent. The present invention furthermore relates to a process for the preparation of the above-mentioned composition, the therapeutic uses thereof, and pharmaceutical compositions containing the nanocomposition according to the invention.

BACKGROUND OF THE INVENTION

Docetaxel, 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}, the compound according to Formula I, is a drug used in cancer chemotherapy.

Formula I

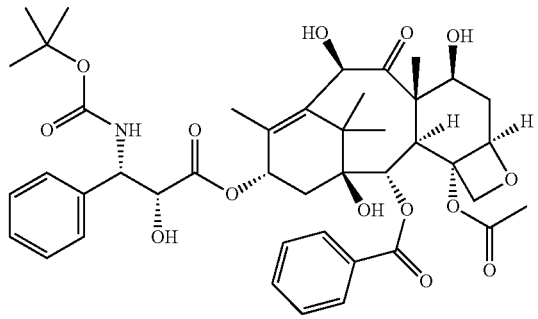

Docetaxel (as generic or under the trade name Taxotere) is a clinically well-established anti-mitotic chemotherapy medication (that is, it interferes with cell division). It is used mainly for the treatment of breast, ovarian, prostate, and non-small cell lung cancer. The main use of docetaxel is the treatment of a variety of cancers after the failure of anthracycline-based chemotherapy. Docetaxel binds to microtubules reversibly with high affinity and has a maximum stoichiometry of 1 mole docetaxel per mole tubulin in microtubules. This binding stabilizes microtubules and prevents depolymerisation from calcium ions, decreased temperature and dilution, preferentially at the plus end of the microtubule. Docetaxel has been found to accumulate to higher concentration in ovarian adenocarcinoma cells than kidney carcinoma cells, which may contribute to the more effective treatment of ovarian cancer by docetaxel. It has also been found to lead to the phosphorylation of oncoprotein bcl-2, which is apoptosis-blocking in its oncoprotein form.

Docetaxel is a cell cycle specific agent, it is cytotoxic to all dividing cells in the body. This includes tumour cells as well as hair follicles, bone marrow and other germ cells. For this reason, common chemotherapy side effects such as alopecia occur; along with certain haematological adverse effects which include Neutropenia and Anaemia in most of the cases, further usual adverse effects of Febrile neutropenia and Thrombocytopenia.

DESCRIPTION OF THE STATE OF THE ART

The problem to be solved in a great number of the chemotherapeutic treatments is the non-specific effect, which means that the chemotherapeutics used is also incorporated in the sane cells and tissues, causing their death. As it can be seen above, the adverse effects of docetaxel cause a limiting factor for the dosing regimen. There is an unmet need to find a composition comprising a carrier and targeting system, which delivers the active compound specifically to the tumour cells, thereby reducing the dose needed, and accordingly, the adverse effects on the intact tissues.

A number of attempts have been made to find a composition which satisfies the above need. U.S. Pat. No. 7,976,825 discloses a macromolecular contrast agent for magnetic resonance imaging Biomolecules and their modified derivatives form stable complexes with paramagnetic ions thus increasing the molecular relaxivity of carriers. The synthesis of biomolecular based nanodevices for targeted delivery of MRI contrast agents is also described. Nanoparticles have been constructed by self-assembling of chitosan as polycation and poly-gamma glutamic acids as polyanion. Nanoparticles are capable of Gd-ion uptake forming a particle with suitable molecular relaxivity. There is no active agent and therapeutic use disclosed in U.S. Pat. No. 7,976,825.

U.S. Pat. No. 8,007,768 relates to a pharmaceutical composition of the nanoparticles composed of chitosan, a negatively charged substrate, a transition metal ion, and at least one bioactive agent for drug delivery. The nanoparticles are characterized with a positive surface charge configured for promoting enhanced permeability for bioactive agent delivery. The pharmaceutical composition consists of a shell portion that is dominated by positively charged chitosan and a core portion, wherein the core portion consists of the positively charged chitosan, a transition metal ion, one negatively charged substrate, at least one bioactive agent loaded within the nanoparticles, and optionally a zero-charge compound. The composition may contain at least one bioactive agent selected from the group of exendin-4, GLP-1, GLP-1 analog, insulin or insulin analog. Docetaxel is not mentioned among the possible active agents.

WO2007019678 relates to an implantable device comprising a biocompatible and biodegradable matrix impregnated with a bioactive complex suitable for selectively targeting the lymphatic system, wherein the bioactive complex comprises one or more particle forming materials and among other bioactive agents e.g. docetaxel. The implantable device according to the document comprises a biocompatible and biodegradable matrix impregnated with a bioactive complex suitable for selectively targeting the lymphatic system, wherein the bioactive complex comprises one or more particle forming materials and one or more bioactive agents. The particles are microparticles or nanoparticles or their combination of microparticles and nanoparticles and the particle size is from about 0.3 μm to about 11.2 μm. Unlike our invention, there is no targeting agent in the above-mentioned composition, and the specific effect is attempted to be achieved by implantation.

US2006073210 relates to a method of enhancing intestinal or blood brain paracellular transport configured for delivering at least one bioactive agent in a patient comprising administering nanoparticles composed of [gamma]-PGA and chitosan. The administration of the nanoparticles takes place orally. The chitosan is a low molecular weight chitosan (50 kDa) and dominates on a surface of said nanoparticles. The surface of said nanoparticles is characterized by a positive surface charge. The nanoparticles have a mean particle size between about 50 and 400 nanometers and are formed via a simple and mild ionic-gelation method. The nanoparticles are loaded with a therapeutically effective amount of at least one bioactive agent. In the above-mentioned prior art document docetaxel is not mentioned as possible therapeutically active agent. Furthermore, though the composition may enhance the penetration of the blood brain carrier, targeting of the therapeutics has not been solved by the invention.

WO06042146 relates to conjugates comprising a nanocarrier, a therapeutic agent or imaging agent and a targeting agent. Among others, the use of polyglutamic acid, chitosan or combinations thereof as nanocarriers, for the delivery of gadolinium as a contrast agent, or for delivering docetaxel or paclitaxel as chemotherapeutic agents is described. According to the document, the use of gadolinium serves solely diagnostic purposes, complexing agent is not used to increase the stability of the nanoparticles, and so the use of metal ions to increase the rate of nanoparticles' penetration into targeted cells is not disclosed.

The state of the art failed to solve the above-mentioned problem that is the reduction of the adverse effects of docetaxel through the decrease of the incorporated active agent by its targeted delivery. There is an unsatisfied need to provide for a stable composition for the targeted therapeutic treatment of tumours using docetaxel. We performed systematic research in the field and, as a result of our surprising findings, completed our invention.

BRIEF DESCRIPTION OF THE SEVERAL VIEW OF THE DRAWINGS

FIG. 1: Size distributions by intensity. This figure shows the size distribution of docetaxel-loaded nanoparticles by intensity in which nanocarriers were constructed by self-assembly of biopolymers at a concentration of 0.3 mg/ml, at given ratios, where the CH-EDTA solution was added into the PGA-FA-DOCE solution.

Figure 2A:
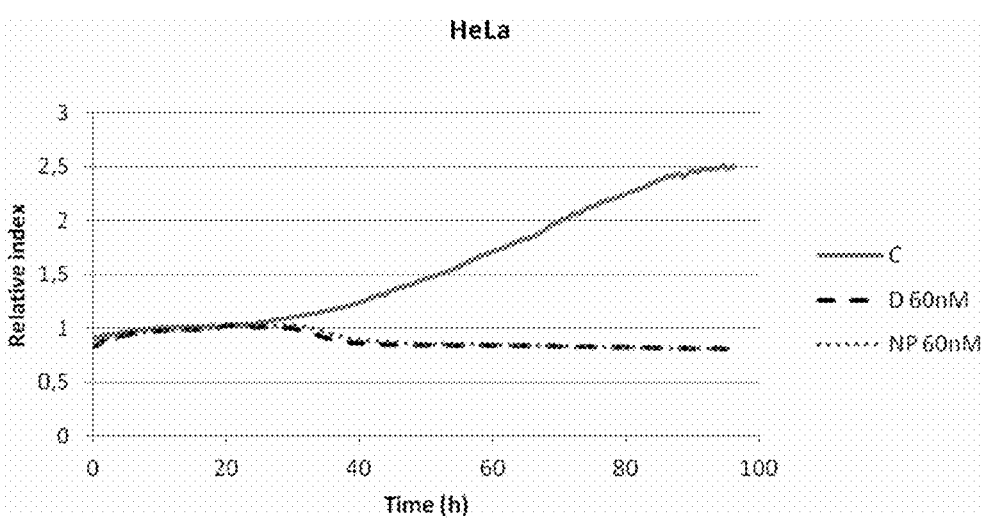
Figure 2B:
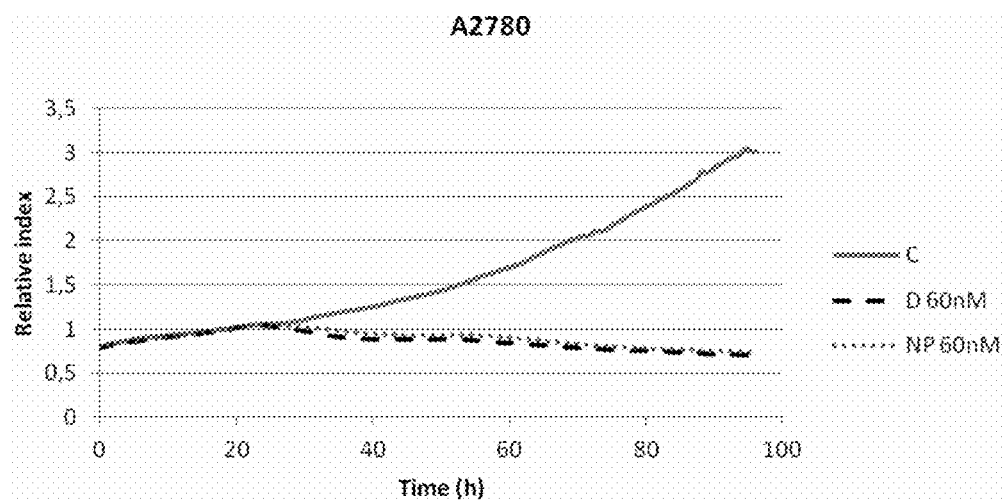
Figure 3A:
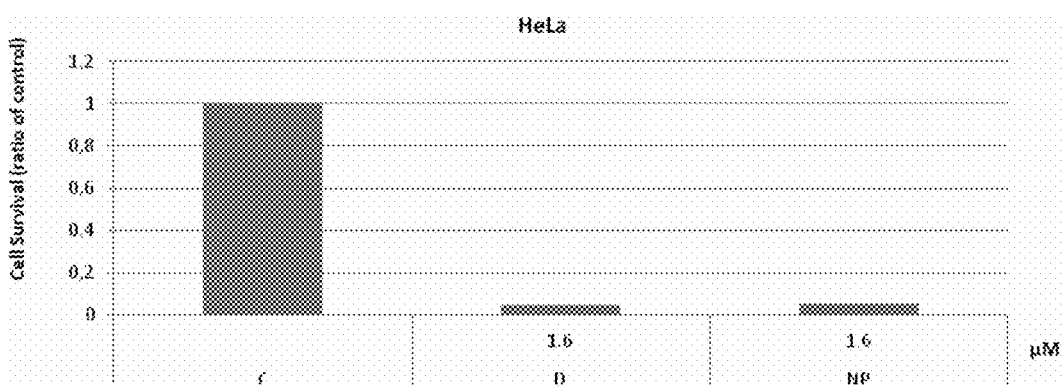
Figure 3B:
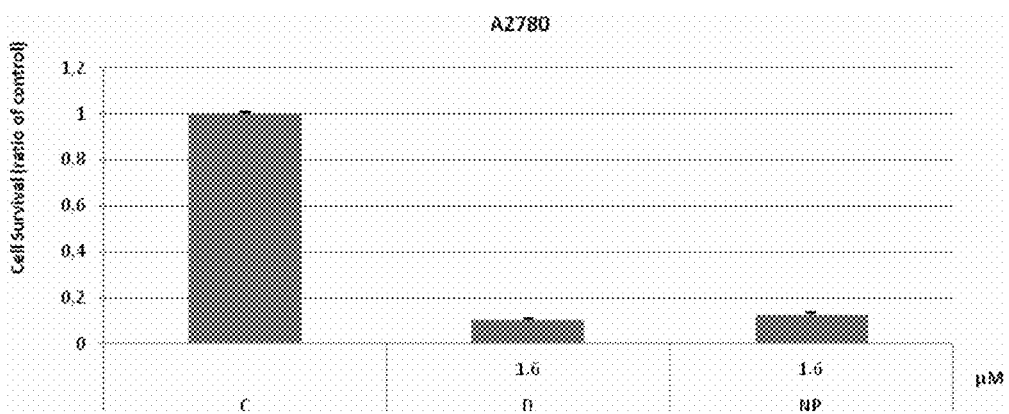
Figure 3C:
Figure 3D:
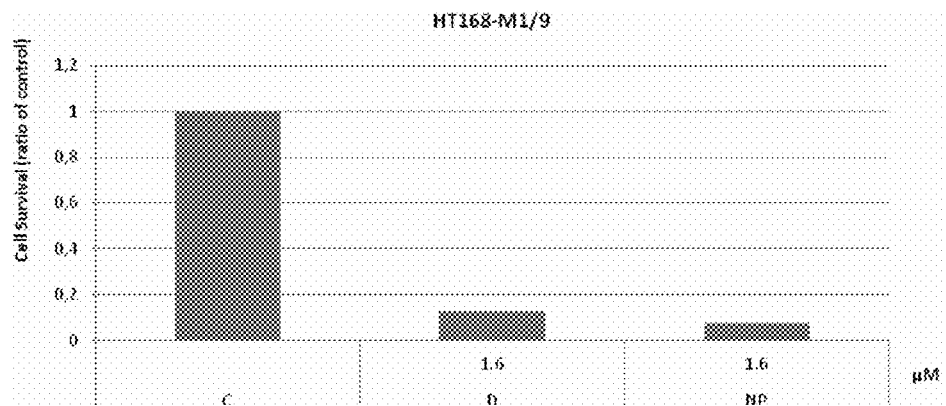
Figure 4A:
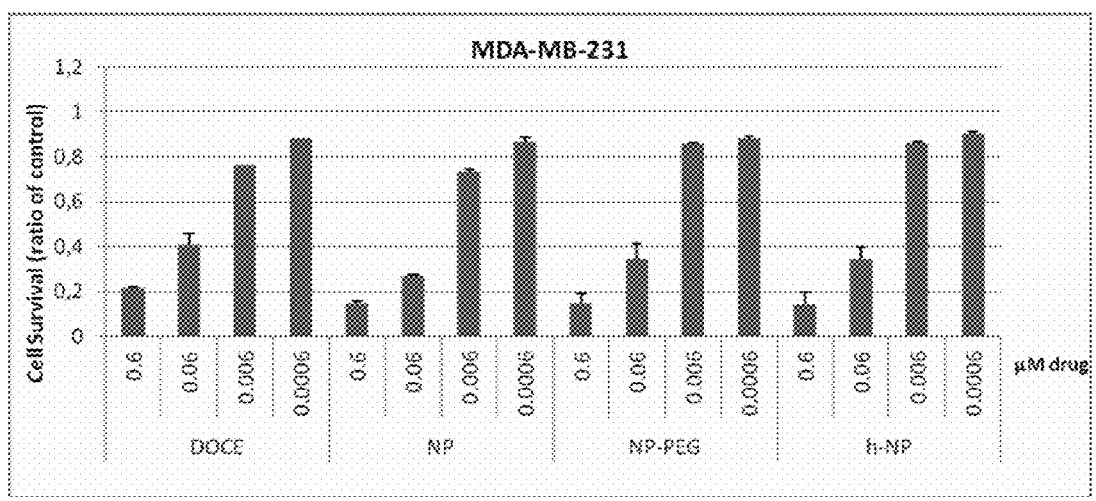
Figure 4B:
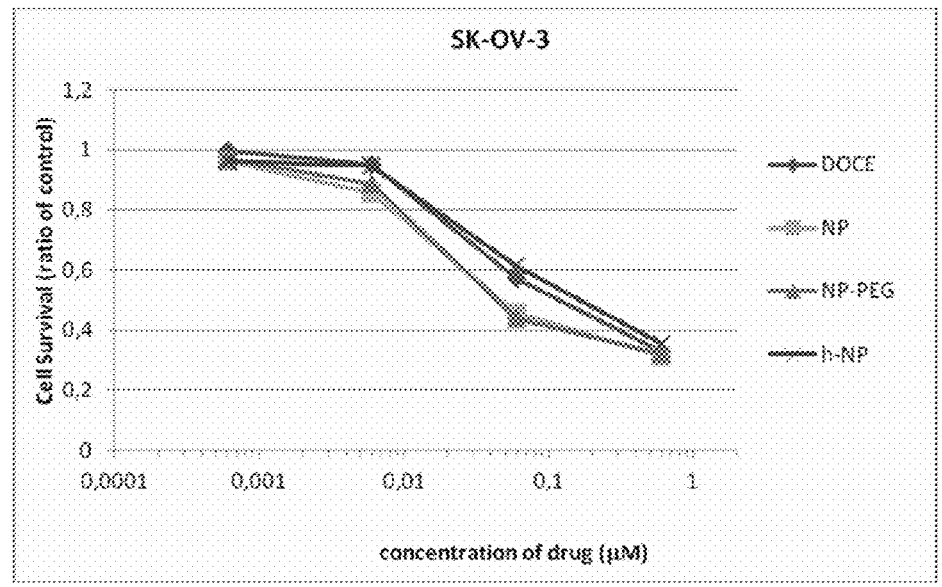
Figure 4C:
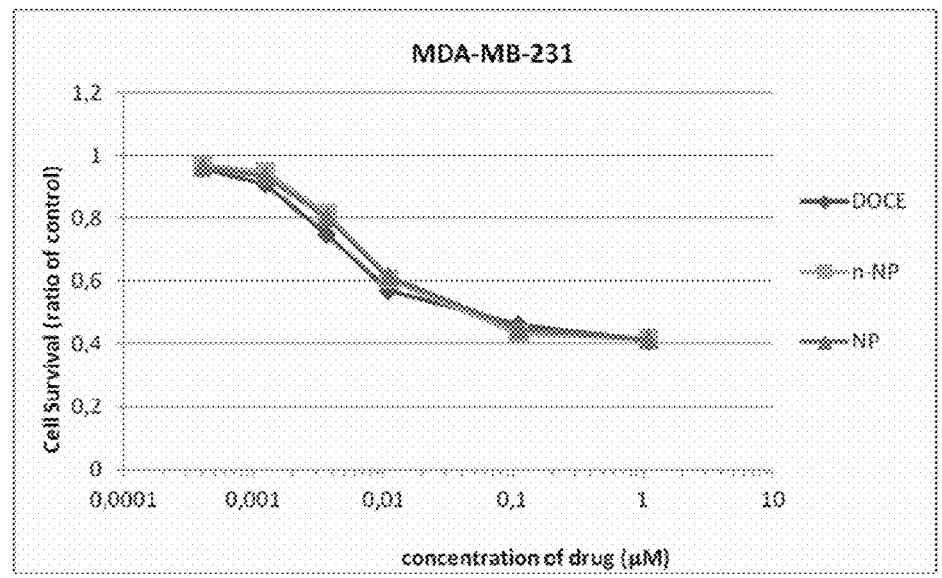
Figure 4D:
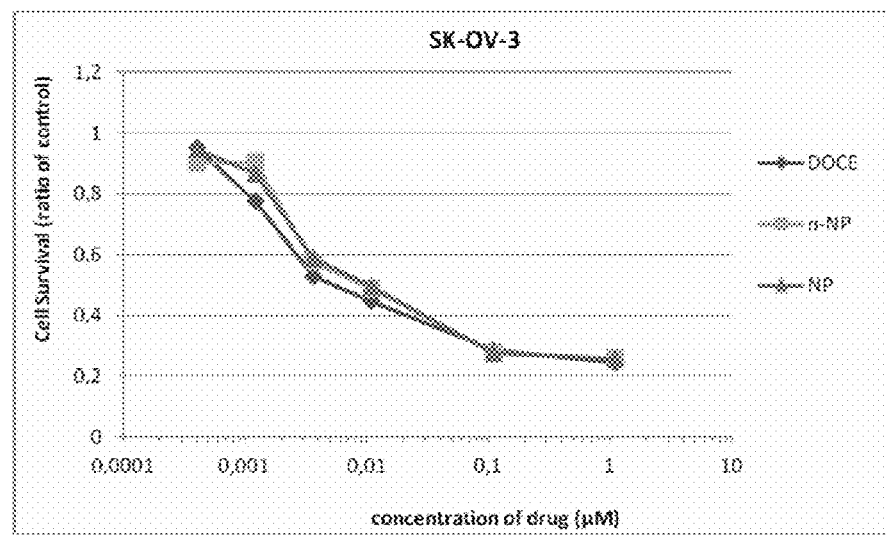

FIG. 2A, 2B: HeLa and A2780 measured by Real Time Analyser (Roche). These figures show the growth profile of HeLa cells (A), and A2780 cells (B) after treating with docetaxel drug molecules (D), docetaxel-loaded nanoparticles (NP) and control cells (C). The injected volume contained the same concentration of docetaxel.

FIG. 3A, 3B, 3C, 3D, 4A, 4B, 4C, 4D: MTT results. FIG. 3 shows the MTT assay results of docetaxel drug molecules (D) and docetaxel-loaded nanoparticles (NP) using HeLa cell line (A), A2780 cell line (B) HT29 cell line (C) and HT168-M1/9 cell line. FIGS. 4A to 4D show the MTT assay results of the cell survival as a function of the drug concentration.

Figure 5:
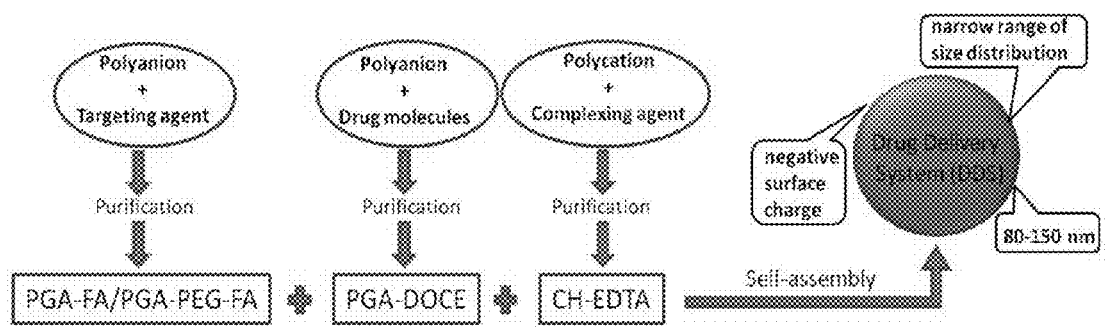

FIG. 5: exemplary steps of docetaxel encapsulation

Figure 6:
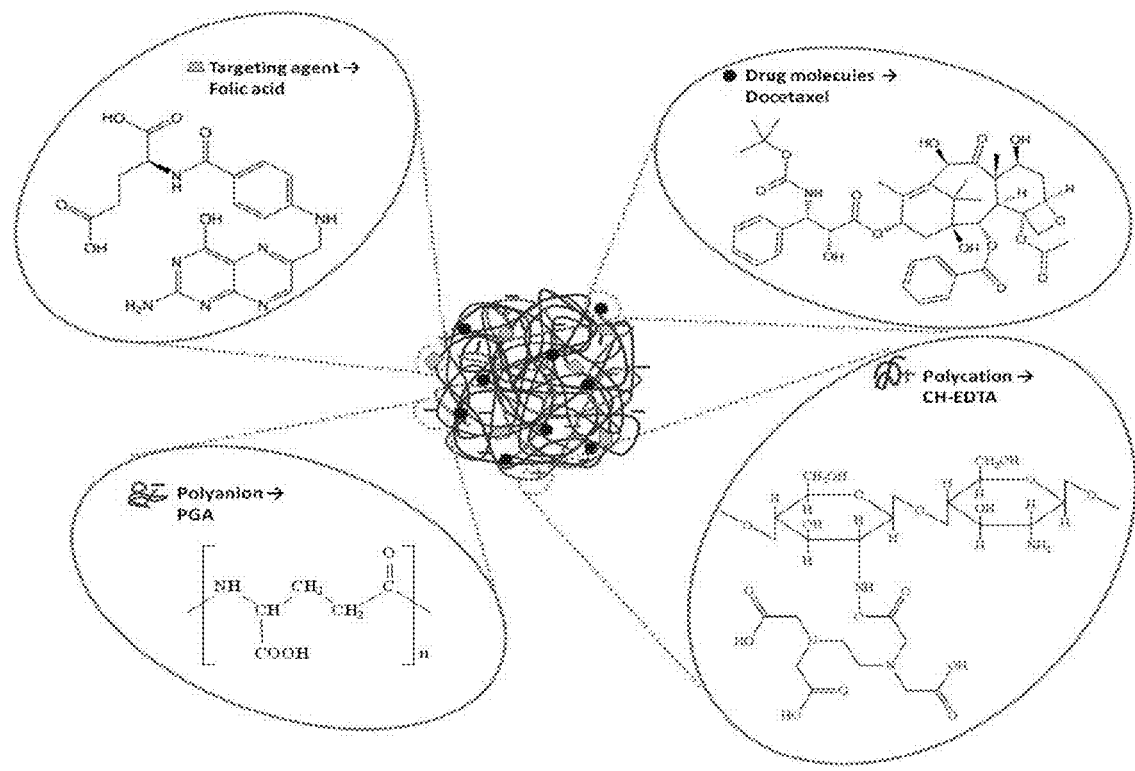

FIG. 6: Components of the docetaxel loaded nanoparticles

DETAILED DESCRIPTION OF THE INVENTION

We have surprisingly found that a stable, self assembling nanocomposition may be prepared by using a polycation together with a polyanion when preparing the carrier of the pharmaceutically active agent. The nanocarrier system according to the present invention consists of at least four components: a polycation, a polyanion, an active agent, which is docetaxel or a derivative thereof, and a targeting molecule, which may be linked to the polycation, the polyanion or both, or to the surface of the nanoparticles. The composition may additionally contain a complexing agent, a metal ion, and a stabilizer/formulating agent, or a PEGylating agent, though these are not necessarily included the composition. The formation of the nanoparticles takes place by the self assembling of the polyelectrolites.

Accordingly, in its first aspect the invention relates to a stable self assembled composition comprising (i) a carrier and targeting system comprising an optionally modified polyanion, and optionally a polycation, which may also be modified; at least one targeting agent which is linked to either the polycation/modified polycation or the polyanion/modified polyanion, or both; or to the surface of the nanoparticle;

(ii) an active compound selected from the group of docetaxel and its pharmaceutically acceptable salts and derivatives especially its hydrates, especially docetaxel trihydrate and docetaxel trihydrate monohydrochloride; and optionally (iii) at least one complexing agent, metal ion and stabilizer/formulating agent.

In a preferred embodiment, the biopolymers are water-soluble, biocompatible, biodegradable polyelectrolyte biopolymers.

One of the polyelectrolyte biopolymers is a polycation, positively charged polymers, which is preferably chitosan or any of its derivatives. In a preferred embodiment in the composition according to the invention the polycation is chitosan, or the modified polycation. In a further preferred embodiment in the composition according to the invention, the modified polycation is selected from the group of CH-DOCE, CH-FA, CH-FA-DOCE, CH-EDTA, CH-DOTA, CH-DTPA, CH-LHRH, CH-RGD.

The other type of the polyelectrolyte biopolymers is a polyanion, a negatively charged biopolymer. Preferably the polyanion is poly-gamma-glutamic acid (PGA); the modified polyanion is selected from the derivatives of PGA, especially PGA-DOCE, PGA-FA, PGA-FA-DOCE, PGA-LHRH, PGA-RGD.

The derivatives of biopolymers can be their cross-linked nanosystems, biopolymer-complexone products, or other grafted derivatives resulted in modifications of biopolymers with other molecules, e.g. PEG oligomers.

Preferably the targeting agent is selected from the group of small molecules, preferably folic acid (FA), peptides, preferably LHRH, RGD, a monoclonal antibody, preferably Transtuzumab.

Preferably the complexing agent is selected from the group of diethylenetriaminepentaacetic acid (DTPA), 1,4,7,10-tetracyclododecane-N,-N',N'',N'''-tetraacetic acid (DOTA), ethylene-diaminetetraacetic acid (EDTA), 1,4,7,10-tetraazacyclododecane-N,N',N''-triacetic acid (DO3A), 1,2-diaminocyclohexane-N,N,N',N'-tetraacetic acid (CHTA), ethylene glycol-bis(beta-aminoethylether) N,N,N',N',-tetraacetic acid (EGTA), 1,4,8,11-tetraazacyclotradecane-N,N', N'',N'''-tetraacetic acid (TETA), and 1,4,7-triazacyclononane-N,N',N''-triacetic acid (NOTA), but is not limited to these materials.

The metal ion is selected from the group of calcium, magnesium, gadolinium, gallium and copper ion; and the stabilizer/formulating agent is selected from the group of glucose, physiological salt solution, PBS, or any combination thereof.

In a preferred embodiment, the drug molecules are ionically or covalently attached to the bioanion or its derivatives via their functional groups.

As used in the present invention the abbreviations below have the following meanings:
PGA means poly-gamma-glutamic acid
PAA means polyacrylic acid
HA means hyaluronic acid
ALG means alginic acid
CH means chitosan
FA means folic acid
LHRH means luteinizing hormone releasing hormone
RGD means arginin-glycin-aspartate amino acid sequence
DOCE means docetaxel
DTPA means diethylene-triamine-pentaacetic acid
DOTA means 1,4,7,10-tetracyclododecane-N,-N',N'',N'''-tetraacetic acid
EDTA means ethylene-diaminetetraacetic acid
DO3A means 1,4,7,10-tetraazacyclododecane-N,N',N''-triacetic acid
CHTA means 1,2-diaminocyclohexane-N,N,N',N'-tetraacetic acid
EGTA means ethylene glycol-bis(beta-aminoethylether) N,N,N',N',-tetraacetic acid
TETA means 1,4,8,11-tetraazacyclotradecane-N,N',N'',N'''-tetraacetic acid
NOTA means 1,4,7-triazacyclononane-N,N',N''-triacetic acid
PEG means poly-ethylene-glycol
PGA-FA means poly-gamma-glutamic acid-bound folic acid
PGA-DOCE means poly-gamma-glutamic acid-bound docetaxel
PGA-FA-DOCE means folic acid-PGA-bound docetaxel
PGA-LHRH means poly-gamma-glutamic acid-bound luteinizing hormone releasing hormone
PGA-RGD means poly-gamma-glutamic acid-bound arginin-glycin-aspartate amino acid sequence
PAA-FA means polyacrylic acid-bound folic acid
PAA-LHRH means polyacrylic acid-bound luteinizing hormone releasing hormone
PAA-RGD means polyacrylic acid-bound arginin-glycin-aspartate amino acid sequence
HA-FA means hyaluronic acid-bound folic acid
HA-RGD hyaluronic acid-bound arginin-glycin-aspartate amino acid sequence
HA-LHRH hyaluronic acid-bound luteinizing hormone releasing hormone
ALG-FA means alginic acid-bound folic acid
ALG-LHRH means alginic acid-bound luteinizing hormone releasing hormone
ALG-RGD means alginic acid-bound arginin-glycin-aspartate amino acid sequence
CH-DOCE means chitosan-bound docetaxel
CH-EDTA-DOCE means CH-EDTA bound docetaxel
CH-EDTA means chitosan-bound ethylene-diaminetetraacetic acid
CH-DOTA means chitosan-bound 1,4,7,10-tetracyclododecane-N,-N',N'',N'''-tetraacetic acid CH-DTPA means chitosan-bound diethylene-triamine-pentaacetic acid
CH-FA means chitosan-bound folic acid
CH-LHRH means chitosan-bound luteinizing hormone releasing hormone
CH-RGD means chitosan-bound arginin-glycin-aspartate amino acid sequence
CH-EDTA-FA means chitosan-bound ethylene-diaminetetraacetic acid and folic acid
CH-FA-EDTA means chitosan-bound folic acid and ethylene-diaminetetraacetic acid
CH-DOTA-FA means chitosan-bound 1,4,7,10-tetracyclododecane-N,-N',N'',N'''-tetraacetic acid and folic acid
CH-FA-DOTA means chitosan-bound folic acid and 1,4,7,10-tetracyclododecane-N,-N',N'',N'''-tetraacetic acid
CH-DTPA-FA means chitosan-bound diethylene-triamine-pentaacetic acid and folic acid
CH-FA-DTPA means chitosan-bound folic acid and diethylene-triamine-pentaacetic acid
EDC*HCl means means (1-ethyl-3-(3-dimethylaminopropyl)-carbodiimide methiodide)
DMSO means dimethyl-sulphoxide
NaOH means sodium-hydroxide
PBS means phosphate buffered saline
1-PAE means 1-phenyl-alanine ethyl ester
PA means polyanion
PC means polycation
PD means docetaxel loaded polymer
NP means nanoparticle
HOBt means 1-hydroxybenzotriazole hydrate
TEA means tryethylamine
MeO-PEG-NH2 means methoxy polyethylene glycol amine
FA-PEG-NH2 means folic acid polyethylene glycol amine
1-PAE-PGA means hydrophobised PGA by 1-phenyl-alanine ethyl ester
PGA-PEG-FA means poly-gamma-glutamic acid bound polyethylene glycol folic acid
PGA-PEG-FA-DOCE means docetaxel loaded PGA-PEG-FA
NP-PEG means pegylated nanoparticles
NP-PEG-FA means nanoparticles bound polyethylene glycol folic acid
h-NP means hydrophobised PGA-based nanoparticles
n-NP means nanoprecipited polyanion-docetaxel based nanoparticles A preferred self-assembled composition according to the present invention is characterized by any one or more of the following features:
(i) the average size of the nanoparticles in swollen state is in the range between 30 to 500 nm, preferably 60 to 200 nm, more preferably about 80 to 120 nm;
(ii) the proportion of the polycation to the polyanion is about 1:20 to 20:1 based on the weight of the agents;
(iii) the polyanion has a pH of 7.5 to 10; a molecular weight of 10 000 Da to 1.5 MDa and a concentration of 0.01 to 2 mg/ml;
(iv) the polycation has a pH of 3.5 to 6; a molecular weight of 60 to 320 kDa and a concentration of 0.01 to 2 mg/ml.

In its second aspect the present invention relates to a process for the preparation of the above mentioned composition according to the invention, characterized in that it comprises the steps of
(i) a targeting agent is bound covalently to the polycation and/or the polyanion, or to the surface of the nanoparticles;
(ii) the active agent is bound by an ionic or a covalently bond to the polycation and/or the polyanion;

(iii) the polycation and the polyanion are contacted with each other, preferably in a ratio of 1:20 to 20:1 based on the weight of the agents, thus are reacted with each other to self-assemble;

(iv) optionally the other components are added to the reaction mixture.

In a preferred embodiment the polyanion used in the process according to the invention has a pH of 7.5 to 10; a molecular weight of 10 000 Da to 1.5 MDa and a concentration of 0.01 to 2 mg/ml; and the polycation used has a pH of 3.5 to 6; a molecular weight of 60 to 320 kDa and a concentration of 0.01 to 2 mg/ml.

Prior to the reaction of the polyelectrolites any one of them or all of them is/are bound to a targeting agent by a covalent bond, thus the nanoparticles will cumulate in the tumourous cells. Furthermore, an active agent according to the present invention is bound to the polycation and/or the polyanion by ionic or covalently bond. It is critical to form such a bond between the active compound and the polycation and/or the polyanion, which is likely to be split by the time of being incorporated in the target cell, and the active compound is released.

On reaction of the polycation and the polyanion a self-assembly takes place, contracting the molecule and resulting in a stable nanosystem. The thus formed nanoparticles possess negative surface charge and a narrow range of size distribution, which ensure the uniform physical and chemical characteristics. The resulting composition is a hydrophilic nanosystem, and forms stable colloid systems in water.

The nanosystem can be designed to achieve compositions with exactly expected features. The type of the self-assembling biopolymers, the order of admixing of the polycation and the polyanion (or their modified derivatives), the molecular weight, the mass ratio, the concentration and the pH of the polycation and the polyanion (or their modified derivatives) will result in different features (size, surface charge, active agent content, targeting agent content, etc.) of the system. The selection of the above elements may be done by the skilled person, knowing the object without undue experimentation.

Furthermore, the present invention relates to a stable self-assembled composition comprising (i) a carrier and targeting system comprising an optionally modified polycation, and an optionally modified polyanion; at least one targeting agent which is linked to either the polycation/modified polycation or the polyanion/modified polyanion, or both; or to the surface of the nanoparticle;

(ii) an active compound selected from the group of docetaxel and its pharmaceutically acceptable salts and derivatives especially its hydrates, especially docetaxel trihydrate and docetaxel trihydrate monohydrochloride; and optionally (iii) at least one complexing agent, metal ion and stabilizer/formulating agent, which is obtainable by the above-mentioned process according to the invention.

In its third aspect the invention relates to a pharmaceutical composition comprising the composition according to the invention together with pharmaceutically acceptable auxiliary materials, preferably selected from group of glucose, physiological salt solution, and PBS, or any combination thereof.

Furthermore, the present invention relates to the use of the composition according to the invention or the pharmaceutical composition according the invention for the preparation of a medicament; and the use of the composition or the pharmaceutical composition according to the invention for the treatment of tumours. Finally the invention relates to a method for the treatment of a subject in need for the treatment of tumours, especially human cervical adenocarcinoma (HeLa, KB), human ovary carcinoma (A2780, SK-OV-3), human lung adenocarcinoma (A549, H1975), human breast carcinoma (Jimt-1, MCF-7, MDA-MB-231), human prostate carcinoma (PC-3, LNCaP), human skin melanoma (HT168-M1/9), human colon adenocarcinoma (HT29), human melanoma (WM983A) and human metastatic melanoma (WM983B) cell line by administering to the subject an effective amount of the composition or the pharmaceutical composition according to the present invention.

EXAMPLES

Preparation of the Formulation According to the Invention

Nanoparticles can be formed by adding polyanion(s) to polycation(s) or the other way round. The addition order of the polyelectrolytes affects the size of the nanoparticles and to a small extent also their surface charge. In both cases the nanoparticle has the structure of a statistical ball, however, significantly smaller particles with narrower size distribution are formed if the polycation (PC) is added to the polyanion (PA).

By using polyanions or polycations of a smaller molar mass, the formed nanoparticle is also smaller. With higher polymer concentration, the size of the formed nanoparticles is also bigger. This may be avoided by the preparation of the nanoparticles in dilute polymer solution, and the solution of the formed nanoparticles with narrow size distribution is then concentrated.

The formed nanoparticles may be coated by PEG. The distribution of the nanoparticles thus obtained differs from the organ-distribution of the non-PEG-ylated nanoparticles. By using the PEG-ylated nanoparticles side effects, e.g. the undesired accumulation of the nanoparticle in the organs, or the amount of the weight-loss may be decreased.

The formed nanoparticles may be coated by a PEG-chain, whish possesses a folic acid at its terminus, thus better targeting may be achieved.

The folic acid content of the polymers and thus the nanoparticles may be increased by coupling the folic acid not directly to the polymers, but rather through a PEG chain. By this method the reaction takes place with higher efficiency.

In all cases PEG with shorter chain, e.g. PEG with 750 Da, 2000 Da, 3400 Da, 5000 Da molecular weight may be used.

Nanoparticles can be formed by nanoprecipitation. In principle, if a hydrophobic polymer is dissolved in an organic solvent that is miscible with water, then this solution is dropped to an aqueous phase with stifling, the polymer will precipitate from the solution in the form of nano-sized particles. The organic solvent (depending from its chemical properties) may be removed by e.g. evaporation, rotation or membrane purification. By decreasing the polymer concentration and/or increasing the volume-proportion of the aqueous phase the size of the formed particles may be decreased. The method is fast, simple and can easily be carried out. The nanoparticles formed are of small site and they have a narrow size distribution.

This nanoprecipitation may be used to encapsulate an active compound, as follows.

1.) The DMSO solution of docetaxel and the acidic form of PGA or pegylated PGA is dropped to water, where the water is the precipitating agent of the acidic form of PGA/PGA-PEG. At this moment the PGA/PGA-PEG precipitates in small sized, spherical particles, while it encloses the molecules of the active agent.

2.) Docetaxel is covalently bound to the acidic form of PGA or pegylated PGA, then the DMSO solution of the purified DOCE-loaded PGA/PGA-PEG is dropped to the aqueous phase. At this moment the docetaxel loaded PGA/PGA-PEG precipitates in small sized, spherical particles.

The particles formed are separated from DMSO by membrane filtration (and the free docetaxel), and reacted with the polycation. In the course of the reaction a self-assembly takes place, which further contracts the particles.

The table below shows the size-modification of the self-assembling nanoparticles at various mixtures of water and DMSO.

|  | Rate of Water:DMSO | Size of nanoprecipited particles (PGA-DOCE) | Size of self-assembled nanoparticles | Final docetaxel conc. (µg/ml) | Final PGA conc. (µg/ml) |
|---|---|---|---|---|---|
| 1. | 10:1 | 595 nm | 101 nm | 19 | 45 |
| 2. | 4:1 | 405 nm | 123 nm | 42 | 100 |
| 3. | 2:1 | 405 nm | 147 nm | 70 | 166 |
| 4. | 1:1 | 439 nm | 176 nm | 105 | 250 |
| 5. | 1:2 | 419 nm | 188 nm | 140 | 333 |

The initial concentration of PGA was 1 mg/ml.

By using lower polymer concentration the size of the PGA-DOCE formed by nanoprecipitation significantly decreases (150-250 nm), however, the size of the nanoparticles formed therefrom decreases only to a minimal extent (80-100 nm).

We can prepare the docetaxel-loaded polyanion by using a hydriphobised polyanion. If PGA is hydrofobised with 1-phenyl-alanine ethyl ester, then after lyophilisation it is dissolved in a water-DMSO mixture. Docetaxel can be dissolved in the DMSO solution of the hydrofobised polymer and can be bound to the polymer without using a tenside.

Tests of the effectiveness of the compositions according to the invention

The internalization and accumulation of the nanosystem according to the present invention were proved on different cell lines in vitro; the cytotoxicity of the nanosystem was tested by investigating the viability of the cells using the MTT method, on among others human cervical adenocarcinoma (HeLa, KB), human ovary carcinoma (A2780, SK-OV-3), human lung adenocarcinoma (A549, H1975), human breast carcinoma (Jimt-1, MCF-7, MDA-MB-231), human prostate carcinoma (PC-3, LNCaP), human skin melanoma (HT168-M1/9), human colon adenocarcinoma (HT29), human melanoma (WM983A) and human metastatic melanoma (WM983B) cell line.

During the MTT tests in some nanosystems modest aggregation was experienced in the microscopic images, which means that some of the compositions in vitro were failed to retain their stability to the expected extent. It was found that the chemical stability of the particles can be improved by adding a complexing agent to one or all of the polymers, thus, aggregation can be avoided, however, in these cases larger particles are formed, and it is a concern that their internalization into the cells is decreasing. This problem may be solved by using a metal ion, especially alkali earth metals, preferably calcium, magnesium, gadolinium, gallium or copper ion, as the system in these cases undergo a contraction.

The effects of glucose, physiological saline solution, infusion base solutions and different buffers on the size, size distribution and stability of the nanoparticles were investigated. It was found that these solutions cause a decrease in the size distribution of the particles and accordingly, their stability will improve.

The xCELLigence RTCA HT Instrument from Roche Applied Science uses gold electrodes at the bottom surface of microplate wells as sensors to which an alternating current is applied. Cells that are grown as adherent monolayers on top of such electrodes influence the alternating current at the electrodes by changing the electrical resistance (impedance). The degree of this change is primarily determined by the number of cells, strength of the cell-cell interactions, interactions of the cells with the microelectrodes and by the overall morphology of the cells. The RTCA Software calculates the Cell Index (CI) as the relative change in measured impedance to represent cell status. The normalized cell index (NCI—plotted on y axis) is the relative cell impedance presented in the percentage of the value at the base-time. NCI shows rate of the surface covered by cells. NCI increases by rise of cell-number or cell-size. For example NCI value in a culture treated with a proliferation inhibitory drug first can increase (because the cell-size grows) and after decreases (because the cell-number reduces)

The MTT test is a colorimetric assay that measures the reduction of yellow 3-(4,5-dimethythiazol-2-yl)-2,5-diphenyl tetrazolium bromide (MTT) by mitochondrial succinate dehydrogenase. The MTT enters the cells and passes into the mitochondria where it is reduced to an insoluble, coloured (dark purple) formazan product. The cells are then solubilised with an organic solvent (dimethyl sulfoxide) and the released, solubilised formazan reagent is measured spectrophotometrically. Since reduction of MTT can only occur in metabolically active cells the level of activity is a measure of the viability of the cells. This method can therefore be used to measure cytotoxicity, proliferation or activation.

Cell Lines:

| Cell line | Type of carcinomacell |
|---|---|
| HeLa | Human cervicaladenocarcinomacell line |
| A2780 | Human ovarycarcinoma cell line |
| SK-OV-3 | Human ovary adenocarcinoma cell line |
| A549 | Human lung adenocarcinoma cell line |
| H1975 | Human lung adenocarcinoma cell line |
| JIMT-1 | Human breastcancer cell line |
| MCF-7 | Human breastcarcinoma cell line |
| PC-3 | Human prostatecarcinoma cell line |
| LNCaP | Human prostatecarcinoma cell line |
| KB | Human cervicalcarcinoma cell line |
| HT168-M1/9 | Human skinmelanoma cell line |
| MDA-MB-231 | Human breastcarcinoma cell line |
| HT29 | Human colon adenocarcinoma cell line |
| WM983A | Human melanoma cell line |
| WM983B | Human metastaticmelanoma cell line |

EXAMPLES

Example 1

Preparation of Folated Poly-Gamma-Glutamic Acid

Poly-gamma-glutamic acid (m=50 mg) was solubilized in water (V=50 ml), then 1-(3-dimethylaminopropyl)-3-ethyl-carbodiimide hydrochloride (EDC*HCl) (m=22 mg) was added to the solution. The mixture was stirred for 30 minutes while cooling on ice. Then 32 mg folic acid dissolved in 10 ml DMSO was added to the reaction mixture and stirred at room temperature in the dark for 24 hours. The folated poly-gamma-glutamic acid was purified by membrane filtration.

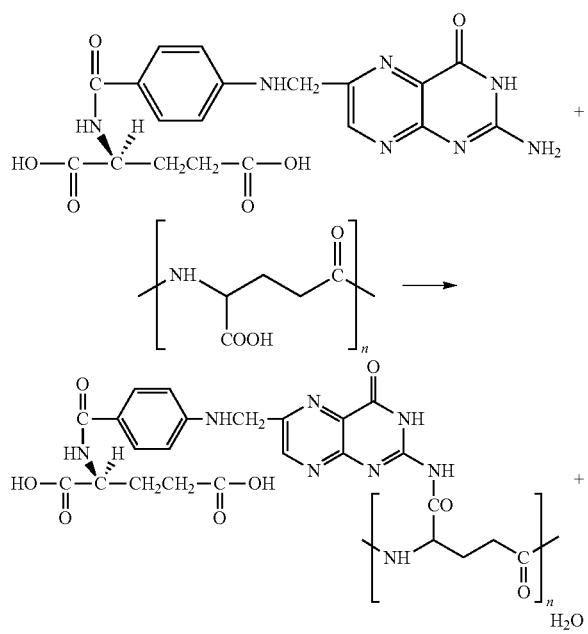

Example 2

Preparation of Folated Chitosan

A solution of 1-(3-dimethylaminopropyl)-3-ethylcarbodiimide hydrochloride (EDC*HCl) and FA in anhydrous DMSO was prepared and stirred at room temperature until FA was well dissolved (1 h). Chitosan was dissolved in 0.1 M hydrochloric acid, to produce a solution with a concentration of 1 mg/ml, and then adjusted to pH 5.5 with 0.10 M sodium hydroxide solution. After the dropwise addition of EDC*HCl (m=5.1 mg in 1 ml distilled water) to the chitosan solution (V=20 ml), the reaction mixture was stirred for 10 min. Then folic acid (m=8.5 mg in dimethyl sulfoxide, V=1 ml) was added to the reaction mixture. The resulting mixture was stirred at room temperature in the dark for 24 h. It was brought to pH 9.0 by drop wise addition of diluted aqueous NaOH and was washed three times with aqueous NaOH, and once with distilled water. The polymer was isolated by lyophilization.

Example 3

Preparation of Chitosan-DTPA Conjugate

Chitosan (m=15 mg) was solubilized in water (V=15 ml); its dissolution was facilitated by dropwise addition of 0.1 M HCl solution. After the dissolution, the pH of chitosan solution was adjusted to 5.0. After the dropwise addition of DTPA aqueous solution (m=11 mg, V=2 ml, pH=3.2), the reaction mixture was stirred at room temperature for 30 min, and at 4° C. for 15 min after that, EDC*HCl (m=8 mg, V=2 ml distilled water) was added dropwise to the reaction mixture and stirred at 4° C. for 4 h, then at room temperature for 20 h. The chitosan-DTPA conjugate (CH-DTPA) was purified by membrane filtration.

Example 4

Preparation of Docetaxel Loaded Poly-Gamma-Glutamic Acid—Ionically Bound

Poly-gamma-glutamic acid (m=2.5 mg) was dissolved in water (V=5 ml) and then adjusted to pH 9.5. The docetaxel was solubilised in ethanol-tween80 (1:1) mixture. Docetaxel (DOCE) solution (V=25 μl) with a concentration of c=20 mg/ml was added to the PGA solution and the reaction was stirred for 24 h at room temperature. The docetaxel-loaded PGA was purified by membrane filtration.

Example 5

Preparation of Docetaxel Loaded Poly-Gamma-Glutamic Acid—Covalently Bound

PGA was dissolved in distilled water (c=0.5 mg/ml, V=20 ml) then 6.3 mg, c=20 mg/ml docetaxel was added to the mixture. The docetaxel was solubilised in ethanol-tween80 (1:1) mixture. The PGA-DOCE mixture was stirred for 30 minutes at room temperature, then for 15 minutes at 4° C. 4.6 mg EDC*HCl was dissolved in 1 ml distillated water and mixed 2.1 mg HOBt dissolved in 1 ml distillated water to produce a mixture. The mixture and 3.1 mg TEA was added to the reaction. The reaction was stirred at 4° C. for 4 hours then room temperature for 20 hours. The docetaxel loaded PGA was purified by membrane filtration.

Example 6

Preparation of Docetaxel Loaded Chitosan—Ionically Bound

Chitosan (m=1.5 mg) was dissolved in 0.01 M hydrochloric acid solution, to produce a solution with a concentration of 0.3 mg/ml, and then adjusted to pH 4.0 with c=0.10 M sodium hydroxide solution. Docetaxel was solubilised in ethanol-tween80 (1:1) mixture. Docetaxel (DOCE) solution (V=20 μl) with a concentration of c=20 mg/ml was added to the chitosan solution and the reaction was stirred for 24 h at room temperature. The docetaxel-loaded chitosan was purified by membrane filtration.

Example 7

Preparation of Targeting, Docetaxel Loaded, Self-Assembled Poly-Gamma-Glutamic Acid/Chitosan Nanoparticles Folated PGA solution (c=0.5 mg/ml) and DOCE-loaded PGA solution (c=0.5 mg/ml) were mixed at a ratio of 1:1. The pH of mixture was adjusted to 9.5. Chitosan was dissolved in water (c=0.5 mg/ml), and the pH was adjusted to 4.0. Chitosan solution (V=1 ml) was added to the PGA mixture (V=2 ml), and was stirred at room temperature for 15 min.

Example 8

Preparation of Targeting, Docetaxel Loaded, Self-Assembled Poly-Gamma-Glutamic Acid/Chitosan Nanoparticles DOCE-loaded PGA solution was prepared with a polymer concentration of c=0.3 mg/ml. The pH of the solution was adjusted to 9.5. Folated chitosan was dissolved in aqueous medium with a concentration of 0.3 mg/ml, and the pH was adjusted to 4.0. Folated chitosan solution (V=1 ml) was added dropwise to the DOCE-loaded PGA solution (V=2 ml) under continuous stirring.

Example 9

Preparation of Targeting, Docetaxel Loaded, Self-Assembled Poly-Gamma-Glutamic Acid/Chitosan Nanoparticles Folated PGA solution was prepared with a polymer concentration of 0.3 mg/ml. The pH of the solution was adjusted to 9.0. DOCE-loaded PGA solution was prepared with a polymer concentration of c=0.3 mg/ml. The pH of the solution was adjusted to 9.5. Chitosan-EDTA was dissolved in aqueous medium with a concentration of 0.3 mg/ml, and the pH was adjusted to 4.0. Folated PGA (V=1.5 ml) was added by dripping to the DOCE-loaded PGA solution (1.5 ml), then 1 ml CH-EDTA solution was added dropwise to the reaction mixture. After 5 minutes of stirring 0.4 ml calcium solution (1 mg/ml) was added by dripping.

Example 9

Characterization of Self-Assembled, Drug-Loaded Nanoparticles

The hydrodynamic size and size distribution of particles was measured using a dynamic light scattering (DLS) technique with a Zetasizer Nano ZS (Malvern Instruments Ltd., Grovewood, Worcestershire, UK). This system is equipped with a 4 mW helium/neon laser with a wavelength of 633 nm and measures the particle size with the noninvasive backscattering technology at a detection angle of 173°. Particle size measurements were performed using a particle-sizing cell in the automatic mode. The mean hydrodynamic diameter was calculated from the autocorrelation function of the intensity of light scattered from the particles. Electrokinetic mobility of the nanoparticles was measured in folded capillary cell (Malvern) with a Zetasizer Nano ZS apparatus.

Example 11

Preparation of Pegylated NP (Pegylation with MeO-PEG-NH$_2$ 2000 Da)

4.65 mg MeO-PEG-NH$_2$ was added dropwise to 15 ml NP ($c_{polymer}$=0.3 mg/ml) and the solution was stirred for 30 minutes at room temperature, then for 15 minutes at 4° C. 1.38 mg EDC*HCl was dissolved in 1 ml distillated water and mixed 0.63 mg HOBt dissolved in 1 ml distillated water to produce a mixture. The mixture and 0.94 mg TEA was added to the reaction. The reaction was stirred at 4° C. for 4 hours then room temperature for 20 hours.

The pegylated NP was purified by membrane filtration.

Example 12

Preparation of NP-PEG-FA (Pegylation with FA-PEG-NH$_2$ 3400 Da)

7.91 mg Fa-PEG-NH$_2$ was added dropwise to 15 ml NP ($c_{polymer}$=0.3 mg/ml) and the solution was stirred for 30 minutes at room temperature, then for 15 minutes at 4° C. 1.38 mg EDC*HCl was dissolved in 1 ml distillated water and mixed 0.63 mg HOBt dissolved in 1 ml distillated water to produce a mixture. The mixture and 0.94 mg TEA were added to the reaction. The reaction was stirred at 4° C. for 4 hours then room temperature for 20 hours. The NP-PEG-FA was purified by membrane filtration.

The results in connection with the targeting of the nanoparticles: when the surface of the nanoparticles was coated with PEG-folic acid of different length, it was experienced that the nanoparticles was more effectively internalized by the cells, as compared to the normal nanoparticles and docetaxel.

Example 13

PEG-Folic Acid Association with PGA

Poly-gamma-glutamic acid (m=300 mg) was solubilized in distilled water (V=300 ml), then HOBt (m=94 mg) was added to the PGA solution. The solution was stirred at 4° C. for 15 minutes, then 1-(3-dimethylaminopropyl)-3-ethylcarbodiimide hydrochloride (EDC*HCl) (m=445 mg in 15 ml distillated water) was added to the solution. The mixture was stirred for 10 minutes while cooling on ice, then folic acid-PEG-amine (NH$_2$-PEGn-NH-FA) (m=100 mg in 10 ml distillated water) and TEA (m=235 mg) was added to the reaction mixture and stirred at room temperature in the dark for 24 hours. The PGA-FA-PEG was purified by membrane filtration.

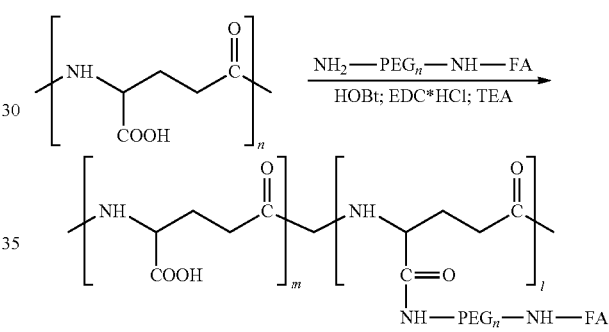

Example 14

Hydrophobisation of PGA with 1-phenylalanine ethyl ester 20 ml 0.5 mg/ml PGA solution was stirred at 4° C. for 30 minutes, then 4.6 mg 1-(3-dimethylaminopropyl)-3-ethylcarbodiimide hydrochloride (EDC*HCl) was added to the solution. The mixture was stirred for 30 minutes, then 1.5 mg 1-phenylalanine ethyl ester was added to the solutions. The reaction was stirred at 4° C. for 4 hours then room temperature for 20 hours. The hydrophobised PGA was purified by membrane filtration and was isolated by lyophilization.

Example 15

Preparation of Docetaxel Loaded Hydrophobised PGA

The lyophilized 1-PAE-PGA was dissolved in distilled water/DMSO mixture (the concentration of the 1-PAE-PGA was 0.5 mg/ml, V=20 ml) then 6.3 mg docetaxel was added to the mixture. The mixture was stirred for 30 minutes at room temperature, then for 15 minutes at 4° C. 4.6 mg EDC*HCl was dissolved in 1 ml distillated water and mixed 2.1 mg HOBt dissolved in 1 ml distillated water to produce a mixture.

The mixture and 3.1 mg TEA was added to the reaction. The reaction was stirred at 4° C. for 4 hours then room temperature for 20 hours.

The docetaxel loaded, hydrophobised PGA was purified by membrane filtration.

Example 16

Nanoprecipitation 1 mg PGA (acidic form) and 1 mg DOCE was solubilised in DMSO, then the solutions were mixed. The final docetaxel and PGA concentration was 1 mg/ml. This mixture was added dropwise to 10 ml distilled water. After that chitosan-EDTA was dissolved in aqueous medium with a concentration of 0.3 mg/ml, and the pH was adjusted to 4.0.

V=535 µl CH-EDTA solution was added dropwise to the reaction mixture.

The formed nanoparticles were purified by membrane filtration.

Example 17

Cellular Uptake of Self-Assembled, Drug-Loaded Nanoparticles

Internalization and selectivity of nanoparticulates was investigated in cultured human cancer cells overexpressing folate receptors by using confocal microscopy and flow cytometry. The samples were imaged on an Olympus Fluo-View 1000 confocal microscope. Excitation was performed by using the 488 nm line of an Ar ion laser (detection: 500-550 nm) and the 543 nm line of a HeNe laser (detection: 560-610 nm) to image Alexa 488 and Alexa 546 respectively. Images were analyzed using Olympus FV10-ASW 1.5 software package. Flow cytometric analysis (BD FACSArray Bioanalyzer System) was carried out with a single-cell suspension, and only the live cells were gated based on forward and side scatter dot plots.

Example 18

MTT Assay of Self-Assembled, DOCE Loaded Nanoparticles

MTT assay of the DOCE-loaded biopolymers and nanoparticles was performed using an UT-6100 Microplate Reader. Approximately 10 000 HeLa cells/well were plated in 96-well plate. The cells were incubated at 37° C. for 24 h. After that the cells were treated with the drug-loaded systems, and incubated at 37° C. for another 24 h. 20 µl MTT reagent was added to each well, and the plate was incubated for 4 h at 37° C. when purple precipitate was clearly visible under microscope, 200 µl DMSO was added to all wells, including control wells. The absorbance of the wells was measured at 492 nm.

In Vivo Results

| Treatment (total dose of 6 injections) | Change in tumor volume (control: 100%) | Change in body weight during the treatment (weight at start: 100%) | Survival proportion at the end of the experiment |
|---|---|---|---|
| Control: 5% glucose | 100% ± 35% | 103% ± 7% | 57% |
| NP (13 mg/kg) | 28% ± 2% | 88% ± 10% | 80% |
| NP-PEG (13 mg/kg) | 39% ± 6% | 92% ± 9% | 100% |
| h-NP (13 mg/kg) | 43% ± 9% | 100% ± 6% | 100% |

The table above summarizes a comparative efficacy study in SK-OV-3 s.c. xenograft SCID mouse model of ovary cancer. Tumor was induced in mice by implanting SK-OV-3 human ovary adenocarcinoma cells s.c. in upperregion of back of SCID mice and allowing the tumors to develop to appreciable size over 21 days (50 mm3). The comparative efficacy study of six i.v. injection (day 21, 28, 35, 42, 49 and 56) of 5% glucose, docetaxel loaded NP 13 mg/kg, docetaxel loaded NP-PEG 13 mg/kg and h-NP 13 mg/kg) was evaluated over 63 days. In this table there are: change in tumor volume of mice on 59th day after tumor in oculation (data represent mean % SEM of five mice per group), change in body weight of mice on 59th day after tumor inoculation (Data represent mean STDEV of five mice per group) and survival proportion at the end of the experiment.

The results of Roche (see FIG. 2) show that the effect of docetaxel and docetaxel-loaded nanoparticles is similar on the studied tumor cell lines; however the nanoparticles due to their targeting ligand deliver the drug molecules into the tumor cells and minimize the side effect of the drug. Effect of drug was studied for several days. The results support that effect of drug is long-drawn, the living cell index did not increase either after 3 days.

Results of MTT assay (see FIGS. 3, 4) confirm that the docetaxel was successfully conjugated and the docetaxel-loaded nanoparticles decreased the cell viability of several tumor cells considerably. The viability of tumor cells was investigated in a function of dose of drug-loaded nanoparticles. It was established that folate-targeted docetaxel-loaded nanoparticles considerably decrease the cell viability depending on the dose of nanoparticles as well as the amount of delivered drug molecules.

The invention claimed is:

1. A stable self-assembled composition comprising
   (i) a carrier and targeting system comprising nanoparticles formed by self-assembly of an optionally modified polyanion, and optionally a polycation, which may also be modified, said nanoparticles having a surface; at least one targeting agent which is linked to the surface of the nanoparticle and to either the polycation/modified polycation or the polyanion/modified polyanion, or both;
   (ii) an active compound selected from the group of docetaxel and its pharmaceutically acceptable salts and derivatives;
   (iii) a PEGylating agent;
   (iv) a complexing agent or a metal ion, or both; and optionally
   (v) a stabilizer/formulating agent,
   wherein the nanoparticles are coated with PEG, and/or PEG-chain containing targeting agent at the end of the chain.

2. The composition according to claim 1, wherein the polycation is selected from the group of chitosan and its derivatives, the modified polycation is selected from the group consisting of CH-DOCE, CH-FA, CH-FA-DOCE, CH-EDTA, CH-DOTA, CH-DTPA, CH-LHRH, CH-RGD; the polyanion is selected from the group consisting of polygamma-glutamic acid (PGA), polyacrylic acid (PAA), hyaluronic acid (HA) and alginic acid (ALG); the modified polyanion is selected from the group consisting of PGA-DOCE, PGA-FA, PGA-FA-DOCE, PGA-LHRH, PGA-RGD, PAA-FA, PAA-LHRH, PAA-RGD, HA-FA, HA-RGD, HA-LHRH, ALG-FA, ALG-LHRH, ALG-RGD; the targeting agent is selected from the group consisting of folic acid (FA), LHRH, RGD, a monoclonal antibody; the complexing agent is selected from the group consisting of diethylenetriaminepentaacetic acid (DTPA), 1,4,7,10-tetracyclododecane-N,-N',N'',N'''-tetraacetic acid (DOTA), ethylene-diaminetetraacetic acid (EDTA), 1,4,7,10-tetraazacyclododecane-N,N',N'''-triacetic acid (DO3A), 1,2-diaminocyclohexane-N,N,N',N'-tetraacetic acid (CHTA), ethylene glycol-bis(beta-aminoethylether) N,N,N',N',-tetraacetic acid (EGTA), 1,4,8,11-tetraazacyclotradecane-N,N', N'',N'''-tetraacetic acid (TETA), and 1,4,7-triazacyclononane-N,N',N''-triacetic acid (NOTA); the metal ion is selected from the group consisting of calcium, magnesium, gadolinium, gallium and copper ion; and the stabilizer/formulating agent is selected from the group consisting of glucose, physiological salt solution, PBS, and any combination thereof.

3. The composition according to claim 1, which is characterized by any one or more of the following features:
 (i) the average size of the nanoparticles is in the range between 30 to 500 nm;
 (ii) the proportion of the polycation to the polyanion is about 1:20 to 20:1 based on their molecular weights;
 (iii) the polyanion has a pH of 7.5 to 10; a molecular weight of 10 000 Da to 1.5 MDa and a concentration of 0.01 to 2 mg/ml;
 (iv) the polycation has a pH of 3.5 to 6; a molecular weight of 60 to 320 kDa and a concentration of 0.01 to 2 mg/ml.

4. A process for the preparation of the composition according to claim 1, characterized in that it comprises the steps of
 (i) a targeting agent is bound covalently to the surface of the nanoparticles and to the polycation and/or the polyanion;
 (ii) the active compound is bound by an ionic or a covalent bond to the polycation and/or the polyanion;
 (iii) the polycation and the polyanion are contacted with each other in a ratio of 1:20 to 20:1 based on their molecular weights, thus are reacted with each other to self-assemble;
 (iv) optionally the other components are added to the reaction mixture.

5. The process according to claim 4, wherein the polyanion used has a pH of 7.5 to 10; a molecular weight of 10 000 Da to 1.5 MDa and a concentration of 0.01 to 2 mg/ml; and the polycation used has a pH of 3.5 to 6; a molecular weight of 60 to 320 kDa and a concentration of 0.01 to 2 mg/ml.

6. A stable self-assembled composition comprising
 (i) a carrier and targeting system comprising nanoparticles formed by self-assembly of an optionally modified polyanion, and optionally a polycation, which may also be modified, said nanoparticles having a surface; at least one targeting agent which is linked to the surface of the nanoparticle and to either the polycation/modified polycation or the polyanion/modified polyanion, or both;
 (ii) an active compound selected from the group of docetaxel and its pharmaceutically acceptable salts and derivatives;
 (iii) a PEGylating agent;
 (iv) a complexing agent or a metal ion, or both, and optionally
 (v) a stabilizer/formulating agent,
 wherein the nanoparticles are coated with PEG, and/or PEG-chain containing targeting agent at the end of the chain, and which composition is obtainable by the process according to claim 4.

7. A pharmaceutical composition comprising the composition according to claim 1 together with pharmaceutically acceptable auxiliary materials.

8. A method for the treatment of a subject in need for the treatment tumours selected from the group consisting of human cervical adenocarcinoma (HeLa, KB), human ovary carcinoma (A2780, SK-OV-3), human lung adenocarcinoma (A549, H1975), human breast carcinoma (Jimt-1, MCF-7, MDA-MB-231), human prostate carcinoma (PC-3, LNCaP), human skin melanoma (HT168-M1/9), human colon adenocarcinoma (HT29), human melanoma (WM983A) and human metastatic melanoma (WM983B) by administering intravenously to the subject an effective amount of the composition according to claim 1.

9. The composition according to claim 1, wherein the active compound is selected from docetaxel hydrates.

10. The composition according to claim 1, wherein the active compound is docetaxel trihydrate.

11. The composition according to claim 1, wherein the active compound is docetaxel trihydrate monohydrochloride.

12. The composition according to claim 2, wherein the monoclonal antibody is Transtuzumab.

13. The composition according to claim 3, wherein the average size of the nanoparticles is in the range between 60 to 200 nm.

14. The composition according to claim 3, wherein the average size of the nanoparticles is in the range between 80 to 120 nm.

15. The composition according to claim 6, wherein the active compound is selected from docetaxel hydrates.

16. The composition according to claim 6, wherein the active compound is docetaxel trihydrate.

17. The composition according to claim 6, wherein the active compound is docetaxel trihydrate monohydrochloride.

18. The composition according to claim 7, wherein the pharmaceutically acceptable auxiliary materials are selected from the group consisting of glucose, physiological salt solution, and PBS, and any combination thereof.

19. The composition according to claim 1, wherein the nanoparticles are coated with PEG-chain containing targeting agent at the end of the chain.

20. The composition according to claim 1, said composition further comprising at least one complexing agent, metal ion and stabilizer/formulating agent.

21. The composition according to claim 1, wherein the active compound is bound ionically or covalently to the polycation and/or the polyanion.

* * * * *